United States Patent
Walter

(10) Patent No.: US 7,173,055 B1
(45) Date of Patent: Feb. 6, 2007

(54) PYRAZOLECARBOXAMIDE AND PYRAZOLETHIOAMIDE AS FUNGICIDE

(75) Inventor: Harald Walter, Rodersdorf (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 413 days.

(21) Appl. No.: 10/149,471

(22) PCT Filed: Nov. 11, 2000

(86) PCT No.: PCT/EP00/11195

§ 371 (c)(1),
(2), (4) Date: Jun. 5, 2002

(87) PCT Pub. No.: WO01/42223

PCT Pub. Date: Jun. 14, 2001

(30) Foreign Application Priority Data

Dec. 9, 1999 (GB) ................... 9929163.5
Dec. 14, 1999 (GB) ................... 9929563.6

(51) Int. Cl.
*A01N 43/56* (2006.01)
*C07D 231/14* (2006.01)

(52) U.S. Cl. ............ 514/406; 514/355; 514/345; 514/348; 514/351; 514/438; 514/445; 514/446; 514/407; 514/424; 514/425; 514/427; 514/428; 514/466; 514/473; 514/617; 514/622; 548/374.1

(58) Field of Classification Search ........ 548/194, 548/369.2, 369.4, 374.1; 514/503, 406, 355, 514/345, 348, 351, 438, 445, 446, 407, 424, 514/425, 427; 504/129, 130, 131, 132, 133, 504/134
See application file for complete search history.

(56) References Cited

U.S. PATENT DOCUMENTS

| | | | | |
|---|---|---|---|---|
| 5,998,450 A | * | 12/1999 | Eicken et al. | 514/355 |
| 6,147,104 A | * | 11/2000 | Eicken et al. | 514/406 |
| 6,350,765 B1 | * | 2/2002 | Schelberger et al. | 514/355 |
| 6,365,608 B1 | * | 4/2002 | Schelberger et al. | 514/352 |
| 6,410,572 B1 | * | 6/2002 | Schelberger et al. | 514/355 |
| 6,436,934 B1 | * | 8/2002 | Schelberger et al. | 514/237.5 |
| 6,489,348 B1 | * | 12/2002 | Schelberger et al. | 514/355 |
| 6,569,875 B1 | * | 5/2003 | Schelberger et al. | 514/355 |
| 6,699,818 B1 | * | 3/2004 | Walter et al. | 504/287 |
| 6,806,286 B2 | * | 10/2004 | Walter et al. | 514/423 |

FOREIGN PATENT DOCUMENTS

| | | |
|---|---|---|
| EP | 0 545 099 | 6/1993 |
| EP | 0 589 301 | 3/1994 |
| WO | WO 93 11117 | 6/1993 |
| WO | WO 97 08148 | 3/1997 |

OTHER PUBLICATIONS

Ishii et al., AN 1990:572014, abstract of JP 02129171.*
Hatanaka et al., AN 1990:478374, abstract of JP 02053775.*

* cited by examiner

*Primary Examiner*—Sabiha N. Qazi
(74) *Attorney, Agent, or Firm*—Rebecca Gegick

(57) ABSTRACT

Novel pyraole derivatives of formula (I), wherein: X is oxygen or sufu, $R_1$ is $C_1$–$C_3$alkyl, $C_1$–$C_3$haloalkyl, $C_1$–$C_3$alkoxy-$C_1$–$C_3$alkyl or $C_1$–$C_3$haloalkoxy-$C_1$–$C_3$alkyl; $R_2$ is $C_1$–$C_3$haloalkyl; and $R_3$ is halogen. The novel compounds have plant-protective properties and are suitable for protecting plants against infestations by phytopathogenic microorganisms.

8 Claims, No Drawings

PYRAZOLECARBOXAMIDE AND PYRAZOLETHIOAMIDE AS FUNGICIDE

The present invention relates to novel pyrazolecarboxamides or pyrazolethioamides which have microbicidal activity, in particular fungicidal activity. The invention also relates to the preparation of these substances, to agrochemical compositions which comprise at least one of the novel compounds as active ingredient, to the preparation of the compositions mentioned and to the use of the active ingredients or compositions in agriculture and horticulture for controlling or preventing infestation of plants by phytopathogenic microorganisms, preferably fungi.

The pyrazolecarboxamides of the present invention have the general formula I

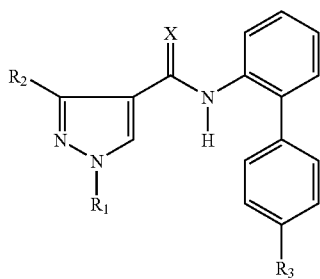

(I)

wherein

X is oxygen or sulfur;

$R_1$ is $C_1$–$C_3$alkyl, $C_1$–$C_3$haloalkyl, $C_1$–$C_3$alkoxy-$C_1$–$C_3$alkyl or $C_1$–$C_3$haloalkoxy-$C_1$–$C_3$alkyl;

$R_2$ is $C_1$, —$C_3$haloalkyl; and $R_3$ is halogen.

Surprisingly, it has now been found that the compounds of formula I exhibit improved biological properties which render them more suitable for the practical use in agriculture and horticulture.

Where asymmetrical carbon atoms are present in the compounds of formula I, these compounds are in optically active form. The invention relates to the pure isomers, such as enantiomers and diastereomers, as well as to all possible mixtures of isomers, e.g. mixtures of diastereomers, racemates or mixture of racemates.

Within the present specification alkyl denotes methyl, ethyl, n-propyl and isopropyl. Alkyl as part of other radicals such as alkoxyalkyl, haloalkyl or haloalkoxyalkyl is understood in an analogous way. Halogen will be understood generally as meaning fluoro, chloro, bromo or iodo. Fluoro, chloro or bromo are preferred meanings. Halogen as part of other radicals such as haloalkyl or haloalkoxyalkyl is understood in an analogous way. Typical alkoxyalkyl radicals include methoxymethyl, ethoxymethyl, propoxymethyl, methoxyethyl, ethoxyethyl and methoxypropyl. Typical haloalkoxyalkyl radicals include fluoromethoxymethyl, difluoromethoxymethyl, trifluoromethoxymethyl, 2,2,2-trifluoroethoxymethyl, 3-chloropro-poxymethyl, 2,2,3,3,3-pentafluoropropoxymethyl, 2,2,2-trifluoroethxyethyl and trifluoromethoxypropyl.

Within the group of compounds of formula I those compounds are preferred wherein X is oxygen (subgroup A).

Another group of compounds of formula I are those wherein X is sulfur (subgroup B).

Within the subgroups A and B those compounds are preferred wherein $R_1$ is $C_1$–$C_3$alkyl; or $R_1$ is $C_1$–$C_3$alkoxy-$C_1$–$C_3$alkyl or $C_1$–$C_3$haloalkoxy-$C_1$–$C_3$alkyl;

$R_2$ is $C_1$–$C_3$haloalkyl; or $R_2$ is $CF_3$, $CF_2H$, $CFH_2$, $CF_2C_1$, $CF_2CF_3$, $CCl_3$, $CH_2CF_3$, $CH_2CCl_3$ or $CF_2CF_2CF_3$; and $R_3$ is fluoro, chloro or bromo (subgroups AC and BD).

Within the subgroup A are those compounds preferred wherein $R_1$ is $C_1$–$C_3$alkyl;

$R_2$ is $C_1$–$C_3$haloalkyl; and $R_3$ is fluoro, chloro or bromo (subgroup A1).

Within the scope of subgroup A1 those compounds of formula I are particularly preferred, wherein $R_2$ is $CF_3$, $CF_2H$, $CFH_2$, $CF_2C_1$, $CF_2CF_3$, $CCl_3$, $CH_2CF_3$, $CH_2CCl_3$ or $CF_2CF_2CF_3$ (subgroup A2).

Another preferred embodiment of compounds of formula I are those within subgroup A, wherein $R_1$ is $C_1$–$C_3$haloalkyl;

$R_2$ is $C_1$–$C_3$haloalkyl; and $R_3$ is fluoro, chloro or bromo (subgroup A3).

A preferred embodiment of compounds of formula I are those within subgroup A, wherein $R_1$ is $C_1$–$C_3$alkoxy-$C_1$–$C_3$alkyl or $C_1$–$C_4$haloalkoxy-$C_1$–$C_3$alkyl;

$R_2$ is $C_1$–$C_3$haloalkyl; and $R_3$ is fluoro, chloro or bromo (subgroup A4).

Within the scope of subgroup B those compounds of formula I are preferred, wherein $R_1$ is $C_1$–$C_3$alkyl;

$R_2$ is $C_1$–$C_3$haloalkyl; and $R_3$ is fluoro, chloro or bromo (subgroup B1).

A special group of compounds of formula I within the scope of subgroup B1 are those, wherein $R_2$ is $CF_3$, $CF_2H$, $CFH_2$, $CF_2C_1$, $CF_2CF_3$, $CCl_3$, $CH_2CF_3$, $CH_2CCl_3$ or $CF_2CF_2CF_3$ (subgroup B2).

Within the scope of subgroup B another preferred embodiment of compounds of formula I are those, wherein $R_1$ is $C_1$–$C_3$haloalkyl;

$R_2$ is $C_1$–$C_3$haloalkyl; and $R_3$ is fluoro, chloro or bromo (subgroup B3).

A preferred embodiment of compounds of formula I are those within subgroup B, wherein $R_1$ is $C_1$–$C_3$alkoxy-$C_1$–$C_3$alkyl or $C_1$–$C_3$haloalkoxy-$C_1$–$C_3$alkyl;

$R_2$ is $C_1$–$C_3$haloalkyl; and $R_3$ is fluoro, chloro or bromo (subgroup B4).

Most preferred within the scope of subgroup AC are those compounds wherein $R_1$ is $CH_3$ or $CH_2OCH_3$; and $R_2$ is $CF_3$, $CF_2H$ or $CFH_2$ (subgroup C).

Particularly preferred within the scope of subgroup C are those compounds wherein $R_1$ is $CH_3$; and $R_2$ is $CF_3$ (subgroup C1).

Another preferred embodiment within the scope of subgroup BD are those compounds wherein $R_1$ is $CH_3$ or $CH_2OCH_3$; and $R_2$ is $CF_3$, $CF_2H$ or $CFH_2$ (subgroup D).

Within the scope of subgroup D are particularly preferred those compounds wherein $R_1$ is $CH_3$; and $R_2$ is $CF_3$ (subgroup D1).

The compounds according to formula I may be prepared according to the following reaction in scheme 1.

carboxamides of formula Ia are preferably obtained by reacting the activated carboxylic acid of formula III with an aromatic amine of formula IV in the presence of a solvent like toluene, benzene, xylene, hexane, cyclohexane chloroform or methylenechloride and in the presence of an acid binding agent like triethylamine, Hünig base, sodium carbonate, potassium carbonate or sodium hydrogencarbonate at a temperature between 0° C. and reflux temperature. The pyrazolethioamides Ib are obtained by reacting the pyrazolecarboxamides Ia with phosphorpentasulfid or Lawesson-reagent in a solvent like dioxane, tetrahydrofurane or toluene at a temperature between 0° C. and reflux temperature. Preferably the entire reaction sequence of scheme 1 is conducted as a single-vessel reaction.

The compounds according to the formula I may also be prepared according to the following reaction in scheme 1A.

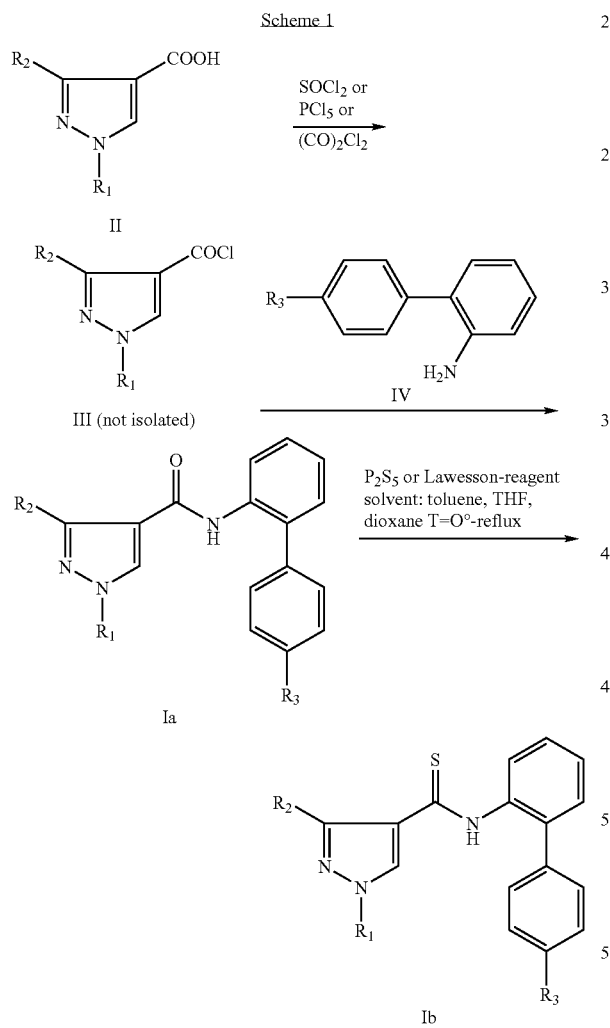

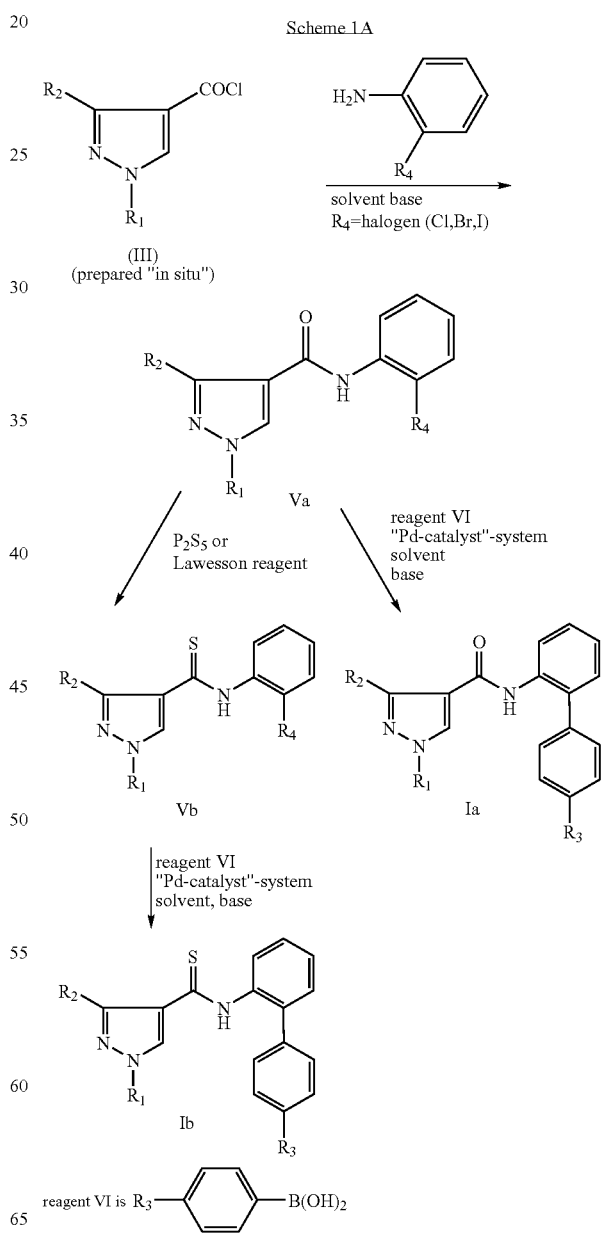

The pyrazole carboxylic acid II reacts with an activating agent such thionyl chloride, phosphorous pentachloride or oxalyl chloride to give the corresponding acid chloride in the presence of a solvent at a temperature between 0° C. and reflux temperature and a reaction time of 30 minutes to 24 hours. Representative solvents are toluene, benzene, xylene, hexane, cyclohexane chloroform or methylenechloride. The obtained acyl chloride III are normally not isolated. The new The "in situ" prepared pyrazole carboxylic acid chloride III reacts with an ortho-halosubstituted phenylamine in the presence of a solvent like toluene, benzene, xylene, hexane, cyclohexane, THF, chloroform or methylenechloride and in the presence of a base like sodium carbonate, sodium hydrogencarbonate, potassium carbonate, Hünig base, triethylamine or pyridine at a temperature between 0° C. and reflux temperature. The obtained pyrazolecarboxamide of formula Va reacts with the p-substituted phenyl boronic acid (VI) in the presence of a Pd-catalyst like Pd(P(phenyl)$_3$)$_4$, Pd(P(phenyl$_3$)Cl$_2$, PdCl$_2$dppb, Pd$_2$(dba)$_3$, Pd(OAc)$_2$, PdOAc$_2$/(o-tolyl)$_3$P, Pd(OAc)$_2$/dppf, Pd(PhCN)$_2$Cl$_2$/Ph$_3$As, Pd(CH$_3$CN)$_2$Cl$_2$, Pd$_2$(dba)$_3$/P(tert.butyl)$_3$, Pd(OAc)$_2$/P(tert.butyl)$_2$biphenyl, Pd(OAc)$_2$/TPPTS, Pd(OAc)$_2$/PCy$_3$, Pd(OAc)$_2$/P(O-i—Pr)$_3$, Pd(OAc)$_2$/2-dimethylamino-2'-dicyclohexylphosphinobiphenyl, Pd(OAc)$_2$/2-dimethylamino-2'-ditert.butylphosphinobiphenyl, Pd(OAc)$_2$/(o-biphenyl)P(cyclohexyl)$_2$ in a solvent like 1,2-dimethoxyethane/water, DMF, DMA, THF/water, dioxane/water, benzene, toluene, xylene and others and a base like sodium carbonate, sodium hydrogencarbonate, potassium carbonate, cesium carbonate, potassium phosphate, triethylamine, sodium hydroxide, sodium ethylate, sodium tert.butylate, silver oxide, barium carbonate, potassium fluoride or cesium fluoride at a temperature between 0° C. and reflux temperature.

The pyrazolethioamide 1b is obtained by treating the pyrazolecarboxamide Va with P$_2$S$_5$ or Lawesson-reagent in a solvent like dioxane, tetrahydrofurane or toluene at a temperature between 0° C. and reflux temperature, giving the pyrazolethioamide Vb and subsequent reaction of this pyrazolethioamide Vb with the boronic acid derivative of formula VI in the presence of a Pd-catalyst like Pd(P(phenyl)$_3$)$_4$, Pd(P(phenyl$_3$)Cl$_2$, PdCl$_2$dppb, Pd$_2$(dba)$_3$, Pd(OAc)$_2$, PdOAc$_2$/(o-tolyl)$_3$P, Pd(OAc)$_2$/dppf, Pd(PhCN)$_2$Cl/Ph$_3$As, Pd(CH$_3$CN)$_2$Cl$_2$, Pd$_2$(dba)$_3$/P(tert.butyl)$_3$, Pd(OAc)$_2$/P(tert.butyl)$_2$biphenyl, Pd(OAc)$_2$/TPPTS, Pd(OAc)$_2$/PCy$_3$, Pd(OAc)$_2$/P(O-i-Pr)$_3$, Pd(OAc)$_2$/2-dimethylamino-2'-dicyclohexylphosphinobiphenyl, Pd(OAc)$_2$/2-dimethylamino-2'-ditert.butylphosphinobiphenyl, Pd(OAc)$_2$/(o-biphenyl)P(cyclohexyl)$_2$ in a solvent like 1,2-dimethoxyethane/water, DMF, DMA, THF/water, dioxane/water, benzene, toluene, xylene and others and a base like sodium carbonate, sodium hydrogencarbonate, potassium carbonate, cesium carbonate, potassium phosphate, triethylamine, sodium hydroxide, sodium ethylate, sodium tert.butylate, silver oxide, barium carbonate, potassium fluoride or cesium fluoride at a temperature between 0° C. and reflux temperature.

The invention relates also to the compounds of the formulae Va and Vb, wherein R$_1$, R$_2$ and X have the meaning as defined for formula I and R$_4$ is halogen, preferably chloro, bromo or iodo.

Compounds of formula IV are known from the literature or may be prepared following the scheme 2.

Scheme 2

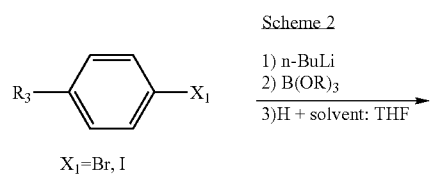

1) n-BuLi
2) B(OR)$_3$
3)H + solvent: THF

X$_1$=Br, I

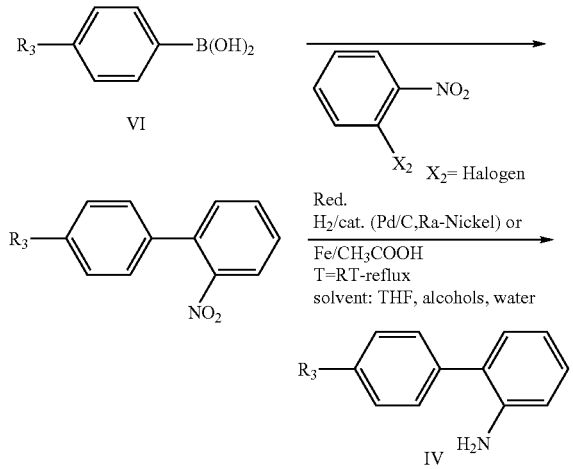

The pyrazoles of formula II are known from the literature or may be prepared following the scheme 3.

Scheme 3

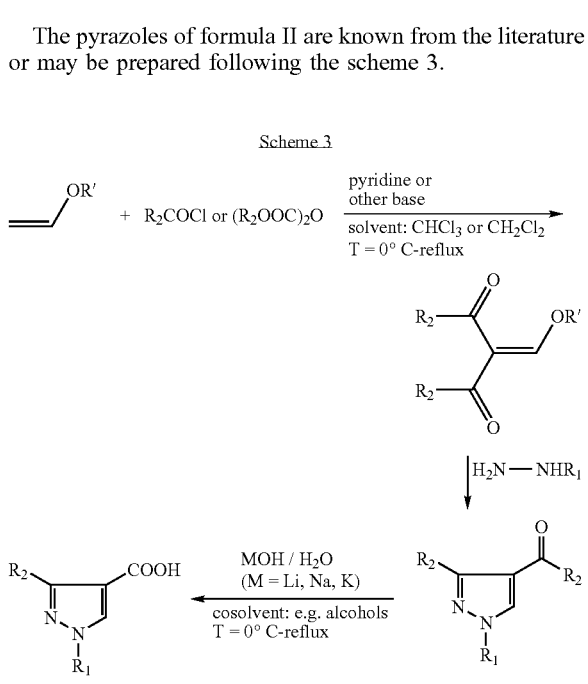

Surprisingly, it has now been found that the novel compounds of formula I have, for practical purposes, a very advantageous spectrum of activities for protecting plants against diseases that are caused by fungi as well as by bacteria and viruses.

The compounds of formula I can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula I can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

The compounds I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I are normally used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula I can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2-[(2-trifluoromethyl)-pyrid-6-yloxymethyl]-3-methoxyacrylate or 2-[α{[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenyl-amino-3,5-dihydroimidazol-4-one (RPA 407213), 3,5-dichloro-N-(3-chloro-1-ethyl-1-methyl-2-oxopropyl)-4-methylbenzamide (RH 7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042), or iprovalicarb (SZX 722).

A preferred method of applying a compound of formula I, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail. Temperatures are given in degrees Celsius. The following abbreviations are used: m.p.=melting point; b.p.=boiling point. "NMR" means nuclear magnetic resonance spectrum. MS stands for mass spectrum. "%" is percent by weight, unless corresponding concentrations are indicated in other units.

EXAMPLE 1

1-Methyl-3-trifluoromethyl-1H-pyrazole-4-carboxylic acid (4'-chlorobiphenyl-2-yl) amide

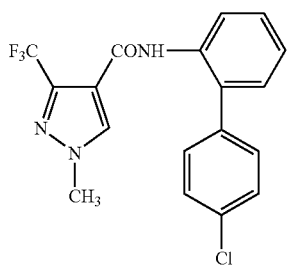

A solution of 1-methyl-3-trifluoromethyl-1H-pyrazole-4-carboxylic acid (0.68 g) and oxalyl chloride (0.49 g) in methylene chloride (30 ml) is stirred for 2 hours at room temperature in the presence of a catalytic amount of DMF. The resulting acid chloride solution is then added to a solution of 4'-chlorobiphenyl-2-ylamine (0.71 g) and triethylamine (0.36 g) in 15 ml of methylene chloride at 0° C. The reaction mixture is then stirred for 4 hours at room temperature. After distilling off the solvent in a water-jet-vacuum, the residue is taken up in ethylacetate/water. The ethylacetate phase is extracted twice with water. After drying of the organic phase with $Na_2SO_4$, the solvent is distilled off in a water-jet-vacuum and the residue purified by column chromatography (silica gel; eluant: ethylacetate/hexane=1:1). 0.8 g of 1-methyl-3-trifluoromethyl-1H-pyrazole-4-carboxylic acid (4'-chlorobiphenyl-2-yl) amide are obtained in the form of slightly brownish crystals having a melting point of 144–146° C.

EXAMPLE 1

Suzuki-Coupling

1-Methyl-3-trifluoromethyl-1H-pyrazole-4-carboxylic acid (4'-chlorobiphenyl-2-yl) amide

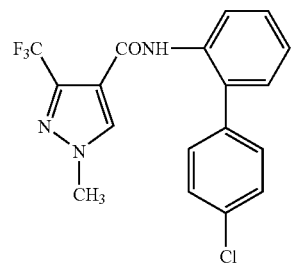

A solution of 1-methyl-3-trifluoromethyl-1H-pyrazole-4-carboxylic acid(2-bromo-phenyl)amide (0.64 g), 4-chlorobenzene boronic acid (0.29 g), powdered sodium carbonate (0.25 g) and tetrakis(triphenylphosphine) palladium (0.04 g) in 25 ml 1,2-dimethoxyethane (DME) and 2 ml water is heated at reflux temperature for 20 hours. After cooling, the solvent is removed in a water jet vacuum and the residue taken up in ethylacetate/water. The ethylacetate phase is washed twice with water and brine and then dried over sodium sulfate. Distilling off the solvent left the raw material which can be further purified by column chromatography (silicagel; eluant: ethylacetate/hexane 1:1) or recrystallization from TBME/hexane. The yield after purification is 0.6 g; m.p.=145–146° C.

The following compounds of formula I are prepared in a similar way, using analogous methods.

TABLE 1

| Compd. No. | $R_1$ | $R_2$ | $R_3$ | X | phys.data m.p. ° C. |
|---|---|---|---|---|---|
| 1 | $CH_3$ | $CF_3$ | Cl | O | 144–146 |
| 2 | $CH_3$ | $CF_3$ | F | O | 149–151 |
| 3 | $CH_3$ | $CF_3$ | Br | O | |
| 4 | $CH_3$ | $CF_3$ | I | O | |
| 5 | $CH_3$ | $CF_2H$ | Cl | O | 161–162 |
| 6 | $CH_3$ | $CF_2H$ | F | O | 144–145 |
| 7 | $CH_3$ | $CF_2H$ | Br | O | |
| 8 | $CH_3$ | $CF_2H$ | I | O | |
| 9 | $CF_3$ | $CF_3$ | Cl | O | |
| 10 | $CF_3$ | $CF_3$ | F | O | |
| 11 | $CH_3$ | $CFH_2$ | Cl | O | |
| 12 | $CH_3$ | $CFH_2$ | F | O | |
| 13 | $CF_2H$ | $CF_3$ | F | O | |
| 14 | $CF_2H$ | $CF_3$ | Cl | O | |
| 15 | $CFH_2$ | $CF_3$ | F | O | |
| 16 | $CFH_2$ | $CF_3$ | Cl | O | |
| 17 | $CH_3$ | $CF_2CF_3$ | F | O | 146 |
| 18 | $CH_2OCH_3$ | $CF_3$ | Cl | O | |
| 19 | $CH_2OCH_3$ | $CF_3$ | F | O | |
| 20 | $CH_2OCF_3$ | $CF_3$ | Cl | O | |
| 21 | $CH_2OCF_3$ | $CF_3$ | F | O | |
| 22 | $CH_3$ | $CF_3$ | Cl | S | 85–86 |

TABLE 1-continued

| Compd. No. | $R_1$ | $R_2$ | $R_3$ | X | phys.data m.p. ° C. |
|---|---|---|---|---|---|
| 23 | $CH_3$ | $CF_3$ | F | S | 125–127 |
| 24 | $CH_3$ | $CF_3$ | Br | S | |
| 25 | $CH_3$ | $CF_3$ | I | S | |
| 26 | $CH_3$ | $CF_2H$ | F | S | |
| 27 | $CH_3$ | $CF_2H$ | Cl | S | |
| 28 | $CH_3$ | $CF_2H$ | Br | S | |
| 29 | $CH_3$ | $CF_2H$ | I | S | |
| 30 | $CF_3$ | $CF_3$ | Cl | S | |
| 31 | $CF_3$ | $CF_3$ | F | S | |
| 32 | $CH_2OCH_3$ | $CF_3$ | Cl | S | |
| 33 | $CH_2OCH_3$ | $CF_3$ | F | S | |
| 34 | $CH_2OCF_3$ | $CF_3$ | Cl | S | |
| 35 | $CH_2OCF_3$ | $CF_3$ | F | S | |
| 36 | $CH_3$ | $CFH_2$ | Cl | S | |
| 37 | $CH_3$ | $CFH_2$ | F | S | |
| 38 | $CH_3$ | $CF_2CF_3$ | F | S | |

TABLE 2

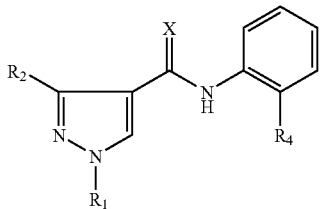

[Va, Vb]

| Compd. No. | $R_1$ | $R_2$ | $R_4$ | X | phys. data m.p. ° C. |
|---|---|---|---|---|---|
| 39 | $CH_3$ | $CF_2H$ | Cl | O | |
| 40 | $CH_3$ | $CF_2H$ | Br | O | |
| 41 | $CH_3$ | $CF_2H$ | F | O | |
| 42 | $CH_3$ | $CF_3$ | Cl | O | 120–121 |
| 43 | $CH_3$ | $CF_3$ | Br | O | 127–128 |
| 44 | $CH_3$ | $CF_3$ | I | O | 176–177 |
| 45 | $CH_3$ | $CF_3CF_2$ | Br | O | |
| 46 | $CH_2OCH_3$ | $CF_2H$ | Cl | O | |
| 47 | $CH_2OCH_3$ | $CF_2H$ | Br | O | |
| 48 | $CH_2OCH_3$ | $CF_2H$ | I | O | |
| 49 | $CH_2OCH_3$ | $CF_3$ | Cl | O | |
| 50 | $CH_2OCH_3$ | $CF_3$ | Br | O | |
| 51 | $CH_2OCH_3$ | $CF_3$ | I | O | |
| 52 | $CH_3$ | $CF_2H$ | Cl | S | |
| 53 | $CH_3$ | $CF_2H$ | Br | S | |
| 54 | $CH_3$ | $CF_2H$ | I | S | |
| 55 | $CH_3$ | $CF_3$ | Cl | S | 107–108 |
| 56 | $CH_3$ | $CF_3$ | Br | S | 109–110 |
| 57 | $CH_3$ | $CF_3$ | I | S | 98–99 |
| 58 | $CH_3$ | $CF_3CF_2$ | Br | S | 102–103 |
| 59 | $CH_2OCH_3$ | $CF_2H$ | Cl | S | |
| 60 | $CH_2OCH_3$ | $CF_2H$ | Br | S | |
| 61 | $CH_2OCH_3$ | $CF_2H$ | I | S | |
| 62 | $CH_2OCH_3$ | $CF_3$ | Cl | S | |
| 63 | $CH_2OCH_3$ | $CF_3$ | Br | S | |
| 64 | $CH_2OCH_3$ | $CF_3$ | I | S | |

Formulation Examples for Compounds of Formula I

Working procedures for preparing formulations of the compounds of formula I such as Emulsifiable concentrates, Solutions, Granulates, Dusts and Wettable powders are described in WO 97/33890.

Biological Examples: Fungicidal Actions

EXAMPLE B-1

Action against *Puccinia* Recondite/Wheat (Brownrust on Wheat)

1 week old wheat plants cv. Arina are treated with the formulated test compound (0.02% active ingredient) in a spray chamber. One day after application wheat plants are inoculated by spraying a spore suspension ($1\times10^5$ uredospores/ml) on the test plants. After an incubation period of 2 days at 20° C. and 95% r. h. plants are kept in a greenhouse for 8 days at 20° C. and 60% r.h. The disease incidence is assessed 10 days after inoculation. Compounds of Table 1 show good activity in this test (<20% infestation). Infestation is prevented virtually completely (0–5% infestation) with compounds 1, 2, 5, 6, 17, 22 and 23.

EXAMPLE B-2

Action against *Podosphaera leucotricha*/apple (Powdery mildew on apple)

5 week old apple seedlings cv. McIntosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r. h. under a light regime of 14/10 h (light/dark) the disease incidence is assessed.

Compounds of Table 1 show good activity in this test. The compounds 1, 2, 5, 6, 17, 22 and 23 exhibit strong efficacy (<20% infestation).

EXAMPLE B-3

Action against *Venturia inaequalis*/apple (Scab on apple)

4 week old apple seedlings cv. McIntosh are treated with the formulated test compound (0.02% active ingredient) in a spray chamber. One day after application apple plants are inoculated by spraying a spore suspension ($4\times10^5$ conidia/ml) on the test plants. After an incubation period of 4 days at 21° C. and 95% r. h. the plants are placed for 4 days at 21° C. and 60% r. h. in a greenhouse. After another 4 day incubation period at 21° C. and 95% r. h. the disease incidence is assessed.

Compounds of Table 1 show good activity in this test. The compounds 1, 2, 5, 6, 17, 22 and 23 exhibit strong efficacy (<20% infestation).

EXAMPLE B-4

Action Against *Erysiphe graminis*/Barley (Powdery Mildew on Barley)

1 week old barley plants cv. Express are treated with the formulated test compound (0.02% active ingredient) in a spray chamber. One day after application barley plants are inoculated by shaking powdery mildew infected plants above the test plants. After an incubation period of 6 days at 20° C./18° C. (day/night) and 60% r. h. in a greenhouse the disease incidence is assessed.

Compounds of Table 1 show good activity in this test. The compounds 1, 2, 5, 6, 17, 22 and 23 exhibit strong efficacy (<20% infestation).

EXAMPLE B-5

Action Against *Botrytis cinerea*/Apple (*Botrytis* on Apple Fruits)

In an apple fruit cv. Golden Delicious 3 holes are drilled and each filled with 30 $\mu$l droplets of the formulated test compound (0.002% active ingredient). Two hours after application 50 $\mu$l of a spore suspension of *B. cinerea* ($4\times10^5$ conidia/ml) are pipetted on the application sites. After an incubation period of 7 days at 22° C. in a growth chamber the disease incidence is assessed.

Compounds of Table 1 show good activity in this test. The compounds 1, 2, 5, 6, 17, 22 and 23 exhibit very strong efficacy (<10% infestation).

EXAMPLE B-6

Action Against *Botrytis Cinerea*/Grape (*Botrytis* on Grapes)

5 week old grape seedlings cv. Gutedel are treated with the formulated test compound (0.002% active ingredient) in a spray chamber. Two days after application grape plants are inoculated by spraying a spore suspension ($1\times10^5$ conidia/ml) on the test plants. After an incubation period of 4 days at 21° C. and 95% r. h. in a greenhouse the disease incidence is assessed.

Compounds of Table 1 show good activity in this test. The compounds 1, 2, 5, 6, 17, 22 and 23 exhibit very strong efficacy (<10% infestation).

EXAMPLE B-7

Action Against *Botrytis cinerea*/Tomato (*Botrytis* on Tomatoes)

4 week old tomato plants cv. Roter Gnom are treated with the formulated test compound (0.002% active ingredient) in a spray chamber. Two days after application tomato plants are inoculated by spraying a spore suspension ($1\times10^5$ conidia/ml) on the test plants. After an incubation period of 4 days at 20° C. and 95% r. h. in a growth chamber the disease incidence is assessed.

Compounds of Table 1 show good activity in this test. The compounds 1, 2, 5, 6, 17, 22 and 23 exhibit very strong efficacy (<10% infestation).

EXAMPLE B-8

Action Against *Pyrenophora teres*/Barley (Net Blotch on Barley)

1 week old barley plants cv. Express are treated with the formulated test compound (0.002% active ingredient) in a spray chamber. Two days after application barley plants are inoculated by spraying a spore suspension ($3\times10^4$ conidia/ml) on the test plants. After an incubation period of 2 days at 20° C. and 95% r. h. plants are kept for 2 days at 20° C. and 60% r.h. in a greenhouse. The disease incidence is assessed 4 days after inoculation. Compounds of Table 1 show good activity in this test. The compounds 1, 2, 5, 6, 17, 22 and 23 exhibit strong efficacy (<20% infestation).

EXAMPLE B-9

Action Against *Septoria nodorum*/Wheat (*Septoria* Leaf Spot on Wheat)

1 week old wheat plants cv. Arina are treated with the formulated test compound (0.02% active ingredient) in a spray chamber. One day after application wheat plants are inoculated by spraying a spore suspension ($5\times10^5$ conidia/ml) on the test plants. After an incubation period of 1 day at 20° C. and 95% r. h. plants are kept for 10 days at 20° C. and 60% r.h. in a greenhouse. The disease incidence is assessed 11 days after inoculation. Compounds of Table 1 show good activity in this test. The compounds 1, 2, 5, 6, 17, 22 and 23 exhibit strong efficacy (<20% infestation).

What is claimed is:

1. A pyrazolecarboxamide of formula I

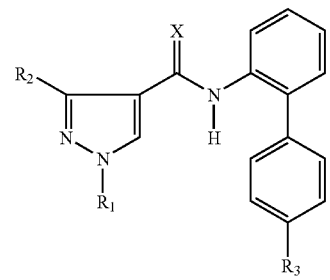

wherein

X is sulfur;

$R_1$ is $C_1$–$C_3$alkyl, $C_1$–$C_3$haloalkyl, $C_1$–$C_3$alkoxy-$C_1$–$C_3$alkyl or $C_1$–$C_3$haloalkoxy-$C_1$–$C_3$alkyl;

$R_2$ is $C_1$–$C_3$haloalkyl; and $R_3$ is halogen.

2. A compound of formula I according to claim 1, wherein $R_1$ is $C_1$–$C_3$alkyl; and $R_3$ is fluoro, chloro or bromo.

3. A compound of formula I according to claim 1, wherein $R_2$ is $CF_3$, $CF_2H$, $CFH_2$, $CF_2CF_3$, $CCl_3$, $CH_2CF_3$, $CH_2CCl_3$ or $CF_2CF_2CF_3$.

4. A compound of formula I according to claim 1, wherein $R_1$ is $C_1$–$C_3$haloalkyl; and $R_3$ is fluoro, chloro or bromo.

5. A composition for controlling microorganisms and preventing attack and infestation of plants therewith, wherein the active ingredient is a compound as claimed in claim 1 together with a suitable carrier.

6. A method of controlling or preventing infestation of cultivated plants by phytopathogenic microorganisms by application of a compound of formula I as claimed in claim 1 to plants, to parts thereof or the locus thereof.

7. A process for the preparation of the compounds according to claim 1, comprising:

(A) reacting a pyrazole carboxylic acid of the formula:

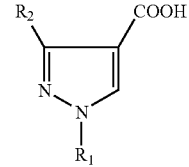

with an activating agent selected from the group consisting of thionyl chloride, phosphorous pentachloride and oxalyl chloride thereby to form a a pyrazole carboxylic acid chloride of the formula:

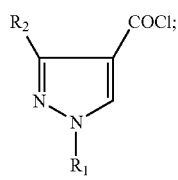

(B) thereafter reacting said a pyrazole carboxylic acid chloride with an aromatic amine of the formula:

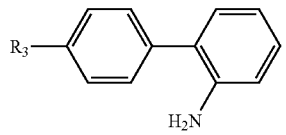

to form a pyrazolecarboxamide of the formula:

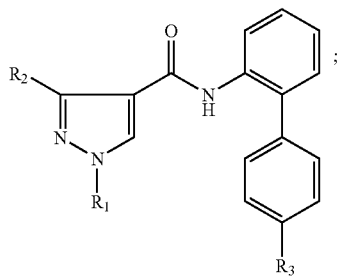

and (C) reacting the pyrazolecarboxamide with a phosphorpentasulfid or Lawesson-reagent in a solvent selected from the group consisting of dioxane, tetrahydrofurane, and toluene at a reaction temperature of between about 0° C. and reflux temperature thereby to form the compounds of formula I in claim 1;

wherein:

$R_1$ is $C_1$–$C_3$alkyl, $C_1$–$C_3$haloalkyl, $C_1$–$C_3$alkoxy-$C_1$–$C_3$alkyl or $C_1$–$C_3$haloalkoxy-$C_1$–$C_3$alkyl;

$R_2$ is $C_1$–$C_3$haloalkyl; and $R_3$ is halogen.

8. A process for the preparation of the compounds according to claim 1, comprising:

(A) reacting a pyrazole carboxylic acid chloride of the formula

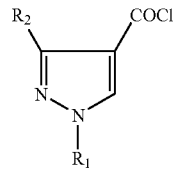

with a substituted phenylamine of the formula:

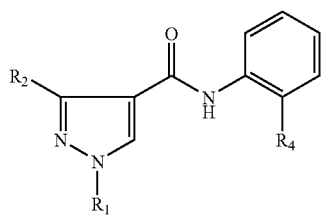

in the presence of a first solvent and a first base thereby to form a pyrazolecarboxamide of the formula:

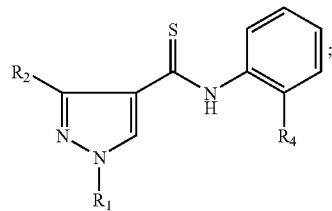

(B) reacting the pyrazolecarboxamide with a phosphorpentasulfid or Lawesson-reagent to form a pyrazolethioamide of the formula:

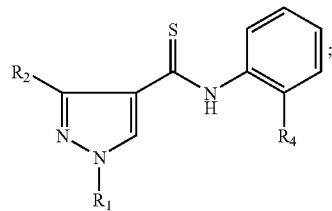

(C) reacting the pyrazolethioamide in the presence of a Pd-catalyst, a second solvent, and a second base thereby to form the compounds of formula I in claim 1; and wherein:

$R_1$ is $C_1$–$C_3$alkyl, $C_1$–$C_3$haloalkyl, $C_1$–$C_3$alkoxy-$C_1$–$C_3$alkyl or $C_1$–$C_3$haloalkoxy-$C_1$–$C_3$alkyl;

$R_2$ is $C_1$–$C_3$haloalkyl;

$R_4$ is chloro, bromo, or iodo.

* * * * *